United States Patent [19]

Karakelle et al.

[11] Patent Number: 4,816,130
[45] Date of Patent: Mar. 28, 1989

[54] BLOOD ELECTROLYTE SENSORS INCLUDING CROSSLINKED POLYETHERURETHANE MEMBRANES

[75] Inventors: Mutlu Karakelle; Richard J. Zdrahala, both of Dayton, Ohio

[73] Assignee: Becton, Dickinson and Company, Franklin Lakes, N.J.

[21] Appl. No.: 133,767

[22] Filed: Dec. 14, 1987

Related U.S. Application Data

[63] Continuation-in-part of Ser. No. 69,453, Jul. 2, 1987, Pat. No. 4,743,629.

[51] Int. Cl.$^4$ ............... G01N 21/00; G01N 27/00; G01N 27/40
[52] U.S. Cl. ............... 204/403; 128/634; 128/635; 204/415; 204/418; 204/433; 357/25; 422/68; 422/83; 436/68; 436/74
[58] Field of Search ............... 128/634, 635; 357/25; 204/415, 403, 433, 418; 422/83, 68; 436/68, 74

[56] References Cited

U.S. PATENT DOCUMENTS

| Re. 31,879 | 5/1985 | Lübbers et al. | 436/133 |
|---|---|---|---|
| 4,020,830 | 5/1977 | Johnson et al. | 204/418 X |
| 4,123,589 | 10/1978 | Korlatzki et al. | 428/425 |
| 4,131,604 | 12/1978 | Szycher | 528/79 |
| 4,200,110 | 4/1980 | Peterson et al. | 128/634 |
| 4,321,333 | 3/1982 | Alberino et al. | 521/159 |
| 4,344,438 | 8/1982 | Schultz | 128/634 |
| 4,371,684 | 2/1983 | Quiring et al. | 528/65 |
| 4,505,799 | 3/1985 | Baxter | 204/416 |
| 4,534,355 | 8/1985 | Potter | 128/635 |
| 4,534,356 | 8/1985 | Papadakis | 128/635 |
| 4,536,274 | 8/1985 | Papadakis et al. | 294/433 |
| 4,615,340 | 10/1986 | Cronenberg et al. | 128/635 |
| 4,638,346 | 1/1987 | Inami et al. | 357/25 |
| 4,672,970 | 6/1987 | Uchida et al. | 128/635 |

OTHER PUBLICATIONS

Donald J. Lyman et al., J. Biomed. Mater. Res., vol. 1, pp. 17-26, (1967).
Condensed Chemical Dictionary, Tenth Edition,. G. G. Hawley, ed., Van Nostrand Reinhold Co., 1981, pp. 210, 287.

Primary Examiner—G. L. Kaplan
Attorney, Agent, or Firm—Richard E. Brown

[57] ABSTRACT

Partition membranes which are permeable to blood electrolytes fabricated from crosslinked polyetherurethane compositions having from 20 to 50% hard segments. The membranes absorb from 50 to 120% of their dry weight of water and have electrolyte diffusion constants of up to $1 \times 10^{-6} cm^2/sec$. The membranes are included in electrochemical, fiber optic and solid state blood electrolyte sensors to provide blood compatible surfaces and to ensure that blood components deleterious to analysis of electrolyte in the blood remain separated from the sensing elements.

10 Claims, 1 Drawing Sheet

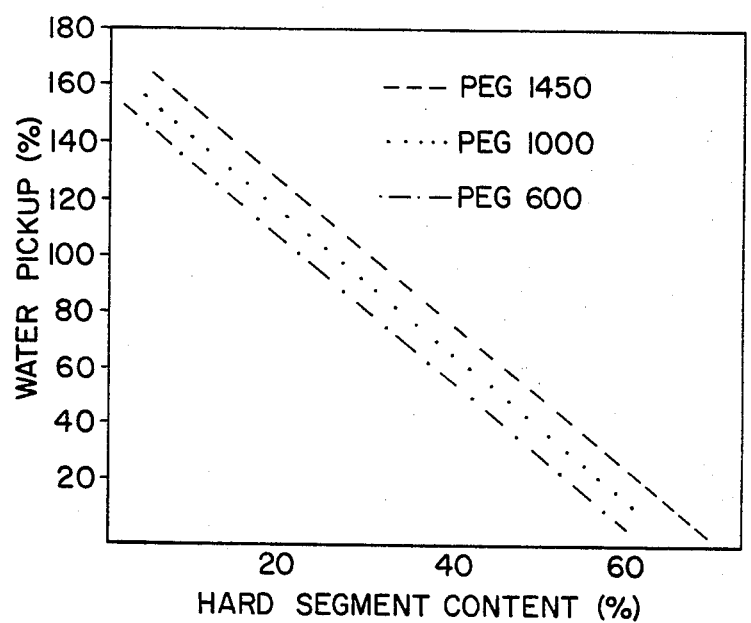

BLOOD ELECTROLYTE SENSORS INCLUDING CROSSLINKED POLYETHERURETHANE MEMBRANES

This application is a continuation-in-part of Ser. No. 069,453 filed July 2, 1987, now U.S. Pat. No. 4,743,629.

BACKGROUND OF THE INVENTION

1. Field of the Invention.

This invention relates to determination of blood electrolytes, and more particularly relates to a permeable membrane prepared from a crosslinked polyetherurethane composition and a blood electrolyte sensing device including the membrane.

2. Background of the Invention.

Thermoplastic polyurethanes to be used as elastomers and the like have been known for a long time. Products prepared from organic compounds having two or more isocyanate groups, high molecular weight polyetherglycols, and low molecular weight diols and diamines as chain extenders are conventionally referred to as polyetherurethanes, and this term, abbreviated PEU, will be used in this disclosure for polyurethanes having a polyether backbone.

PEU compositions develop microdomains conventionally termed hard segments and soft segments, and as a result are often referred to as segmented PEUs. The hard segments form by localization of the portions of the polymer molecules which include the isocyanate and extender components and are generally of high crystallinity. The soft segments form from the polyether glycol portions of the polymer chains and generally are either noncrystalline or of low crystallinity.

PEU formulations having properties such as water absorption and mechanical strength which make them useful for specific applications have been developed. It is also known that these properties are greatly influenced by the choice or ratio of the components of the formulations. For example, Szycher, in U.S. Pat. No. 4,131,604 discloses a PEU molded into a bladder capable of continuous flexing making it useful in heart assist systems. In order to achieve the desired properties, the polyetherglycol component of the composition is limited to polytetramethylene glycol. Alberino et al., in U.S. Pat. No. 4,321,333, discloses that, by using blends of diisocyanates, formulations having significantly improved green strength are obtained. Quiring et al., in U.S. Pat. No. 4,371,684, reports that thermoplastic polyurethanes of improved extrudability are obtained by use of two low molecular weight diol chain extenders instead of the theretofore conventional butanediol.

Lyman et al. (Journal of Biomedical Materials Research 1 17 (1967) discloses dialysis membranes prepared from uncrosslinked PEU by solution casting onto a glass plate.

Sensing devices for determination of blood components are well-known. All such devices utilize a membrane which is permeable to the blood component being analyzed. U.S. Pat. Nos. 4,534,356 and 4,536,274, to Papadakis disclose electrochemical sensors in which membranes useful for blood gas analysis are broadly defined as hydrogels or hydrophilic polymers or copolymers and membranes useful for blood pH determinations are copolymers of fluorine-containing monomers.

A portable assembly for analysis of blood oxygen and carbon dioxide which includes a blood sampler, an electrochemical sensor and blood gas analyzer is disclosed by Kronenberg et al. in U.S. Pat. No. 4,615,340. The sensor includes a gas permeable, ion permeable membrane fabricated of polycarbonate or cellulose and a gas permeable, ion impermeable membrane of polytetrafluoroethylene or polypropylene.

Blood gases are measured by Lübbers et al. in U.S. Pat. No. Re. 31,879 by a fluorescence-based sensor using selective gas permeable membranes and optical fibers to direct incident light to a dye and fluorescence from the dye.

A fiber optic pH probe for physiological studies using an ion permeable cellulose membrane is described by Peterson et al. in U.S. Pat. No. 4,200,110.

Baxter, in U.S. Pat. No. 4,505,799, discloses an ion sensitive field effect transistor (ISFET) for measurement of hydrogen ions which includes a membrane which may be silicon nitride or aluminum oxide.

Potter, in U.S. Pat. No. 4,534,355, shows an electrochemical device for sensing blood oxygen and carbon dioxide having a linear PEU membrane coated onto the mounting of the device. The Potter membrane is disclosed to absorb up to 50% water. On the other hand, Korlatski, in U.S. Pat. No. 4,123,589, describes a PEU membrane which exhibits impermeability to water making it useful as a food casing.

Ionic permeability across a hydrophilic PEU membrane occurs by partitioning ions in a fluid between absorbed water in the membrane and the fluid. Thus, the rate at which an ionic solute crosses a membrane depends on the water content of the membrane i.e., faster transmembrane passage and shorter analysis time may be achieved with membranes of high water absorptivity. The present invention is directed to membranes of exceptionally high water retention which, in addition, retain the mechanical strength necessary for use in blood electrolyte sensing devices.

SUMMARY OF THE INVENTION

One aspect of the present invention is a sensor for a component of a fluid. The sensor includes a sensing element and a membrane. The preferred sensor is a blood electrolyte sensor in which the sensing element is an ion sensitive field effect transistor. A particularly preferred sensor is a blood pH sensor.

Another aspect of the present invention is a semipermeable partition membrane prepared from a crosslinked PEU composition. The composition comprises a diisocyanate, a polyetherglycol, a low molecular weight chain extender and a low molecular weight trifunctional crosslinker. Preferred PEU compositions have from 20-50% hard segment content and are prepared from diphenylmethane-4,4'-diisocyanate (MDI), polyethylene oxide (PEO) or polyetherglycol mixtures containing at least 50% PEO, a chain extending diol of up to 10 carbon atoms, water as an additional chain extender and a crosslinking triol of up to 10 carbon atoms. In the most preferred composition for membrane fabrication, the polyether glycol and crosslinker are PEO having a molecular weight of about 1450 and trimethylolpropane (TMP) respectively, water and 1,4 butane diol (BDO) are chain extenders and the hard segment content is from 30 to 40% of the total weight of the composition.

The membranes of the invention absorb from 50-120% of their dry weight in water, and when saturated with water, exhibit a hydrogen ion diffusion constant of up to $1 \times 10^6$ cm$^2$/sec.

Because of their high degree of adhesiveness to various surfaces, the membranes of the invention may be solution cast onto components of blood sensors whereby blood is precluded from contacting the components. In addition to exhibiting excellent transmembrane diffusion characteristics due to their high water content, the membranes also have excellent mechanical strength making them particularly useful in blood analysis devices wherein the membrane covers a void volume. The membranes do not contain any additives, in particular no polymerization catalysts, whereby they have excellent blood compatibility.

BRIEF DESCRIPTION OF THE DRAWING

The Figure shows the relationship of the hard segment content of the composition of the invention to its water absorbing capacity.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The present invention provides a membrane fabricated from a chemically crosslinked PEU formulation which absorbs 50% or more by weight, of water. The invention embraces, but is not limited to, blood electrolyte sensing devices, preferably pH sensors, which include such membranes.

Known blood electrolyte sensors are of three basic types, electrochemical, fiber optic and solid state, and the invention contemplates inclusion of any known sensor which may be adapted to include the membrane of the invention. Exemplary of, but not limited to, such sensors are electrochemical sensors as described in U.S Pat. Nos. 4,536,274 and 4,615,340; fluorescence sehsors as described in U.S. Pat. Nos. 4,200,110 and Re. 31,879; and ISFET sensors as described in U.S. Pat. No. 4,505,799. The disclosures in these patents are herin incorporated by reference.

Sensing assemblies generally include a sensor having a sensing element capable of generating a detectable signal. Exemplary of sensing elements are dyes which fluoresce or change color in the presence of an electrolyte, electrodes which sense changes in potential and solid state transistors which sense a change in the amperage or voltage of an electrical current. Also included in most sensing assemblies are a membrane and apparatus to transmit a signal generated by the element to a data display or analyzer. The membrane generally is selected to be permeable to a substance being sensed but substantially impermeable to substances which may be deleterious to the sensing element or which may interfere with accurate signal generation.

The membranes of the present invention are particularly suitable for inclusion in sensing assemblies for detection or measurement of water soluble components of a fluid which may diffuse across the membrane. Most preferably, the membrane may be included in a blood analysis assembly. Exemplary of blood components amenable to sensing with the membranes of the invention are gases such as oxygen and carbon dioxide, solutes such as glucose, uric acid, urea and the like, and electrolytes such as ions of hydrogen, potassium, sodium, lithium and chlorine. Preferred components for analysis using the membrane of the invention are blood electrolytes, most preferably, blood hydrogen ions.

PEU compositions suitable for fabrication of the membranes of the present invention include four essential components, a diisocyanate, a polyether glycol, a chain extender, and a low molecular weight triol crosslinker. Preferred compositions include water as an additional extender.

Suitable diisocyanates are aromatic diisocyanates such as diphenylmethane-4,4'-diisocyanate, (MDI), diphenylmethane-3,3'-diisocyanate, alicyclic diisocyanates such as isophorone diisocyanate and dicyclohexylmethane-4,4'-diisocyanate, and aliphatic diisocyanates, as, for example, hexamethylene diisocyanate. The most preferred diisocyanate is MDI.

The polyether glycol component may be polyethylene oxide (PEO), alone or mixed with polypropylene oxide or polybutylene oxide. The preferred polyol is polyethylene oxide having a molecular weight of from about 600 to 3300, or a mixture containing 50% or more by weight thereof. The most preferred polyetherglycols are polyethylene oxides having average molecular weights of 1000 and 1450.

The chain extender may be water and/or a low molecular weight branched or unbranched diol, diamine or aminoalcohol of up to 10 carbon atoms or mixtures thereof. Representative nonlimiting examples of chain extenders are BDO; ethylene glycol; diethylene glycol; triethylene glycol; 1,2-propanediol; 1,3-propanediol; 1,6-hexanediol; 1,4-bis-hydroxymethyl cyclohexane, hydroquinone dihydroxyethyl ether, ethanolamine, ethylenediamine and hexamethylenediamine. Preferred chain extenders are 1,6-hexanediol, ethylenediamine, hexamethylenediamine and, most preferably, water and BDO.

The crosslinker may be a low molecular weight multifunctional compound having three or more hydroxyl and amine groups and 10 or less carbon atoms. Representative suitable crosslinkers are TMP, glycerol, pentaerythritol, trimethylolethane, mannitol and the like. Preferred crosslinkers are triols, most preferably TMP.

The percentages of the components may be such that the hard and soft segments of the composition may be from about 20 to 50% and from about 50-80%, preferably from about 30 to 40% and 60 to 70% respectively of the total weight of the formulation. The molar ratio of crosslinking extender to linear extender may be from about 100 to 0.01, preferably from about 20 to 0.05, and the molar ratio of polyetherglycol to the combined chain extender and crosslinker may be from about 0.1 to 10.

From these percentages and ratios, suitable proportions of the components may readily be calculated. Derived formulas (1) and (2) below may also be used to determine suitable proportions of the components.

The PEU compositions of the invention may be prepared by the conventional two step or prepolymer method. As an example of this procedure, the hydroxyl containing components, i.e., the extender, crosslinker and polyether glycol may be reacted in a suitable solvent as, for example, dimethylformamide or preferably dimethylacetamide (DMAC) with approximately two equivalents of diisocyanate so that each hydroxyl group is reacted with a diisocyanate molecule giving a prepolymer having isocyanate terminal groups (a process conventionally referred to as capping). An example of a typical prepolymer procedure is given in Example I, however, various modifications of this conventional procedure are well-known to those skilled in the art.

The prepolymer molecules may then be further chain extended by reaction between their terminal isocyanate groups and water and/or the low molecular weight diol and, if desired, further crosslinked, preferably concurrently with chain extension, by reacting the prepolymer isocyanate groups with the low molecular weight triol.

A feature of the method for preparing the PEU formulations of the invention is that the polymers are prepared from the components without adding a polymerization catalyst. Conventional catalysts in the art, for example, organometallic compounds such as dibutyl tin dilaurate, are leachable and may cause deleterious effects in blood-contacting elements fabricated from prior art catalyst-containing PEU. By avoiding use of a catalyst, PEUs of the invention are purer and less toxic than those of the prior art.

The membranes of the invention may be from 0.001 to 0.5, preferably from 0.01 to 0.1 mm thick, and representative procedures for their preparation are given in Examples II and III. Preparation of membranes from polymeric compositions is conventional in the art, and the methods of preparation of the membranes of the invention do not constitute a part of this invention.

Membranes prepared from representative nonlimiting PEU formulations of the invention are given in Table I wherein the components are given in weight percent of the final prepolymer.

TABLE I

| MDI | PEO (ave MW) | TMP | BDO | water | % water absorption* | D (cm²sec)** |
|---|---|---|---|---|---|---|
| 37.4 | 60 (1000) | 1.3 | — | 1.3 | 59.7 | $4.6 \times 10^{-9}$ |
| 37.4 | 59.9 (1000) | 0.7 | 0.7 | 1.3 | 60.0 | $6.9 \times 10^{-9}$ |
| 36.6 | 61.1 (1000) | 0.3 | 0.8 | 1.3 | 61.0 | $7.6 \times 10^{-9}$ |
| 32.1 | 65 (1450) | 0.1 | 1.6 | 1.2 | 97.6 | $3.6 \times 10^{-6}$ |

*as determined in Example IV
**diffusion constant, as determined in Example V

In accordance with the present invention, it has been found that the membranes prepared from the compositions of the invention absorb from 50–120% of their dry weight of water. Several compositional factors acting together are believed to account for this property. The FIGURE shows that for any given hard segment content, increasing polyether glycol molecular weight from 600 to 1450 increases water pickup by about 15%. The FIGURE also shows that, at constant polyether glycol molecular weight, decreasing hard segment content from 50% to 20% increases water pickup from 50% to 120%. It is believed, although as yet unsubstantiated, that the increase in water pickup consequent to decreasing hard segment content is due to reduced crystallinity in the polymer composition.

The membranes of the invention have excellent transmembrane ion diffusion properties. It has been found that the hydrogen ion diffusion content increases linearly with decreasing hard segment content. The diffusion constants of representative membranes of the invention are given in Table I.

The approximate water absorption and diffusion constant for any crosslinked PEU membrane of the invention may be predicted from formulas (1) and (2) below, derived as given in Example VI. Conversely, the formulas may be used to approximate the quantities of one or more of the components needed to prepare a membrane of the invention having a desired water absorption or diffusion constant.

$$W = 152.03 + 1.65 \times 10^{-2} M_n - 2.54 \, HS - 8.60 \times 10^{-4} M_x \quad (1)$$

$$D = 1.54 \times 10^{-8} - 1.46 \times 10^{-13} M_n - 2.49 \times 10^{-10} HS - 1.37 \times 10^{-13} M_x \quad (2)$$

In formulas (1) and (2), W is percent water pick-up, D is diffusion constant, HS is percent hard segment, $M_n$ is PEO molecular weight and $M_x$ is molecular weight between crosslinks. The term $M_x$ in the formulas is obtained from formula (3):

$$M_x = \frac{\text{total weight of polymer batch}}{\text{moles of TMP}} \times 1.5 \quad (3)$$

EXAMPLE I

General Procedure for Prepolymer Synthesis

Polyethylene oxides were obtained from Union Carbide Corporation and used as received after determining the hydroxyl number and water content by the phthalic anhydride-pyridine method and Karl Fisher titration respectively and adjusting stoichiometry accordingly.

BDO (obtained from GAF) and TMP (obtained from Celanese) were used as is.

MDI was filtered at about 52° C. and vacuum stripped until cessation of bubbling before use.

PEO, BDO and TMP were combined in a resin bottle at 60° C., vacuum stripped for 30 minutes at 4–5 mm Hg and diluted with an equal part by weight DMAC previously stored over 4A molecular sieves. The mixture was cooled to ambient temperature and two equivalents of MDI, based on the total hydroxyl content, was added dropwise, followed by addition of a quantity of DMAC equal to ½ part by weight of the MDI. The mixture was stirred for about four hours at 50° C. to complete prepolymer formation.

EXAMPLE II

Preparation of Membranes

Membranes of 5 mil thickness were prepared by casting the PEO-polyurethane prepolymer in DMAC from Example I onto clean, untreated glass plates using an adjustable clearance Gardner knife (Gardner Labs) set at 10 mil wet film clearance. The membranes were then stored on the glass plates at ambient conditions, usually 1–3 days, during which time chain extension with atmospheric moisture took place and the membranes formed non-tacky surfaces. Residual solvent was flashd off (one hour, 70° C., vacuum oven). The membranes were then soaked in deionized distilled water (24 hours), removed from the glass plate and dried to constant weight in a vacuum oven at 60° C. Membranes prepared in this way were used for water pickup and permeability determinations.

EXAMPLE III

Membrane Application to a Sensor

An ion sensitive field effect transistor pH electrode is mounted in conventional fashion on a catheter through a side hole. The catheter is coated by dipping into the prepolymer solution of Example I until the coating is of the desired thickness. The catheter is maintained at ambient conditions for chain extension by atmospheric water for 24 hours, then dried in a vacuum oven at 60°–70° C. for 24 hours to remove solvent.

EXAMPLE IV

Determination of Water Pickup

Five 2×2 inch samples from each membrane were immersed in distilled water for 24 hours at 30.0°±0.1° C. At these conditions, an equilibrium water take-up was achieved. The membranes were then removed from containers, and the surface water was carefully blotted with filter paper without applying pressure. Each membrane sample was placed into a tared, air-tight glass vial and weighed. The samples in the vials were then vacuum dried at 60°±2° C. (4–5 mm Hg) for 24 hours and reweighed. The percent water pick-up and the degree of swelling were calculated from weight difference data using the following equation:

$$W = (W_s - W_p/W_p) \times 100$$

where W is percent water pick-up, $W_s$ is weight of the swollen membrane and $W_p$ is weight of the dry membrane.

EXAMPLE V

Determination of Membrane Diffusion Constant

Apparent membrane thickness was first calculated from the weight of dry 7×7 cm membrane sheets assuming average density of 1.15g/cm³. The membrane sheets were then equilibrated in distilled water for 24 hours at ambient temperature prior to testing. For the measurements, a two compartment permeability cell was placed in a constant temperature bath (25.0°±1° C.). Compartment A of the cell was filled with a known volume of $5.0 \times 10^{-3}$M NaCl solution and blanketed with nitrogen gas. A known volume of $5.0 \times 10^{-3}$M HCl solution was placed in compartment B and the pH change in both compartments was measured for 60 minutes using an ORION EA 940 Ionalayzer. The diffusion constant was calculated from the obtained data using Fick's first law of diffusion:

$$J = -D \, dC/dx$$

where J is total flux, D is diffusion constant and dC/dx is concentration gradient across the membrane.

EXAMPLE VI

Formulas (1) and (2) were derived by a statistical analysis, using a 3×3 Greaco-Latin Square experimental design, of experimentally determined values for W and D of the membranes (prepared by the method of Examples I and II) of Table II having preselected values for HS, Mn and the molar ratio (R) of TMP to BDO.

TABLE II

| HS | Mn | R | W | D (cm²/sec) |
|---|---|---|---|---|
| 50 | 1000 | 1 | 35.4 | $2.9 \times 10^{-9}$ |
| 55 | 1450 | 3 | 34.8 | $6.4 \times 10^{-10}$ |
| 60 | 600 | 6 | 8.9 | $1.0 \times 10^{-16}$ |
| 60 | 1450 | 1 | 19.8 | $2.2 \times 10^{-12}$ |
| 50 | 600 | 3 | 19.0 | $9.7 \times 10^{-12}$ |
| 55 | 1000 | 6 | 21.0 | $3.0 \times 10^{-11}$ |
| 55 | 600 | 1 | 13.3 | $1.5 \times 10^{-12}$ |
| 60 | 1000 | 3 | 12.9 | $1.0 \times 10^{-16}$ |
| 50 | 1450 | 6 | 48.0 | $2.2 \times 10^{-9}$ |

Thus, the invention discloses crosslinked PEU membranes of exceptionally high water absorptivity and ion diffusion constants. The membranes retain excellent mechanical strength and are useful in electrolyte sensing devices.

What is claimed is:

1. A sensor for blood analysis comprising a sensing element for an electrolyte in a blood stream and a crosslinked polyetherurethane membrane permeable to said electrolyte but impermeable to other components of said blood stream so that, when the sensor is in the blood stream, the membrane prevents contact between said sensing element and said other components, said membrane comprising a crosslinked polyetherurethane composition having a hard segment of from 20 to 50%, said composition comprising a product from the reaction of a diisocyanate, polyethylene oxide, a chain extending diol of from 2 to 10 carbon atoms and a trihydroxy crosslinking agent of 2 to 10 carbon atoms, said membrane absorbing from 50 to 120% of its dry weight of water, said sensing element being capable of generating a detectable signal in response to contact with said electrolyte.

2. The sensor of claim 1 wherein said sensing element comprises a fluorescent dye.

3. The sensor or claim 2 wherein said signal is fluorescence.

4. The sensor of claim 1 wherein said sensing element comprises an electrode.

5. The sensor of claim 4 wherein said signal is a change in an electrode potential sensed by said electrode.

6. The sensor of claim 1 wherein said sensing element is an ion-sensitive solid state transistor.

7. The sensor of claim 6 wherein said signal is a change in amperage of an electrical current sensed by said transistor.

8. The sensor of claim 6 wherein said signal is a change in voltage of an electrical current sensed by said transistor.

9. The sensor of claim 1 wherein said electrolyte is selected from the group consising of an ion of sodium, potassium, lithium, calcium, chlorine and hydrogen.

10. A sensor for blood analysis comprising a sensing element which includes a field effect transistor sensitive to the pH of a blood stream and a crosslinked polyetherurethane membrane being capable of absorbing from 50–120% of its dry weight of water, said membrane being permeable to hydrogen ions in a blood stream but impermeable to other components of said blood stream so that, when the sensor is in the blood stream, the membrane prevents contact between said transistor and said other components, said membrane comprising a crosslinked polyetherurethane composition having a hard segment of from 20 to 50%, said composition comprising a product from the reaction of a diisocyanate, polyethylene oxide, a chain extending diol of from 2 to 10 carbon atoms and a trihydroxy crosslinking agent of 2 to 10 carbon atoms, said transistor being capable of generating a detectable signal consequent to a contact with said hydrogen ions.

* * * * *